United States Patent [19]
Wong et al.

[11] Patent Number: 5,780,058
[45] Date of Patent: Jul. 14, 1998

[54] ORAL DELIVERY OF DISCRETE UNITS

[75] Inventors: Patrick S.-L. Wong, Palo Alto; Howard B. Rosen, Los Gatos; Nathan Roth, San Francisco; Phyllis I. Gardner, Stanford, all of Calif.

[73] Assignee: ALZA Corporation, Palo Alto, Calif.

[21] Appl. No.: 684,602

[22] Filed: Jul. 19, 1996

[51] Int. Cl.⁶ .................................................. A61K 9/24
[52] U.S. Cl. .......................... 424/473; 424/438; 424/451; 424/464
[58] Field of Search ................... 424/473, 438, 424/451, 464

[56] References Cited

U.S. PATENT DOCUMENTS

| | | | |
|---|---|---|---|
| 2,436,505 | 2/1948 | DuRall | 128/222 |
| 2,867,536 | 1/1959 | Mead et al. | 99/138 |
| 3,610,483 | 10/1971 | Visconti et al. | 222/478 |
| 3,845,770 | 11/1974 | Theeuwes et al. | 128/260 |
| 3,995,631 | 12/1976 | Higuchi et al. | 128/260 |
| 4,034,756 | 7/1977 | Higuchi et al. | 128/260 |
| 4,111,202 | 9/1978 | Theeuwes | 128/260 |
| 4,320,759 | 3/1982 | Theeuwes | 128/260 |
| 4,327,725 | 5/1982 | Cortese et al. | 128/260 |
| 4,449,983 | 5/1984 | Cortese et al. | 604/892 |
| 4,581,013 | 4/1986 | Allen | 604/78 |
| 4,765,989 | 8/1988 | Wong et al. | 424/473 |
| 4,792,333 | 12/1988 | Kidder | 604/83 |
| 4,981,468 | 1/1991 | Benefiel et al. | 604/83 |
| 5,110,597 | 5/1992 | Wong | 424/438 |
| 5,123,915 | 6/1992 | Miller et al. | 606/234 |
| 5,222,940 | 6/1993 | Wilk | 604/77 |
| 5,223,259 | 6/1993 | Lackney | 424/435 |
| 5,391,381 | 2/1995 | Wong | 424/473 |

FOREIGN PATENT DOCUMENTS 1906964  2/1969  Germany.

OTHER PUBLICATIONS

Kikendall, MD et al. *Digestive Diseases and Sciences*, vol. 28, No. 2 (Feb. 1983). "Pill–Induced Esophageal Injury".

*Primary Examiner*—D. Gabrielle Brouillette
*Attorney, Agent, or Firm*—John A. Dhuey; Steven F. Stone

[57] ABSTRACT

The present invention is directed to an oral active agent delivery system and method for delivering discrete units of an active agent formulation to a patient. An active agent formulation chamber (10) containing the active agent formulation and having a fluid passing active agent formulation retainer (14) is placed at one end (16) into a fluid and at a second end (18) into a patient's mouth. The active agent is delivered when the patient sips on the end of the chamber.

15 Claims, 4 Drawing Sheets

ORAL DELIVERY OF DISCRETE UNITS

FIELD OF THE INVENTION

The present invention is related to the oral delivery of an active agent. More particularly, it is method and device for oral delivery of an active agent formulation in the form of discrete units mixed with a fluid, by inserting the discrete units into a hollow active agent formulation chamber. A retainer in a first end of the chamber prevents the release of the discrete units from the first end of the chamber while allowing for fluid flow when suction is applied at the second end of the chamber. The discrete units can easily be swallowed in admixture with the fluid drawn through the chamber.

BACKGROUND OF THE INVENTION

Tablets, capsules, caplets and many other types of devices have been used for oral delivery of active agents. These forms are relatively easy to manufacture and convenient for use in the hospital or other institutional settings or at home. Many different types of active agents have been incorporated into such dosage forms—ranging from analgesics to antibiotics to hormones.

There are patients that, because of age or infirmity, have difficulty swallowing solid oral dosage forms. According to Kikendall et al., *Digestive Diseases and Sciences* 28:2 (1983), there were 221 cases documented between 1970–1982 of tablet and capsule induced oesophageal injury. The most commonly implicated drugs were tetracycline (108 cases), emepromium bromide (36 cases), potassium chloride (16 cases) and ferrous salts (12 cases).

In view of the above, there exists a need for oral dosage forms where swallowing of a large solid system is avoided that are easy to use and manufacture.

U.S. Pat. No. 2,436,505 to DuRall describes a pill douser for administering medicines in liquid form or in pills or tablets. The device has a bowl at the top for containing the medicine and a tube that can be submerged in a liquid held in a drinking glass. The liquid is drawn upward for administering the liquid and any pill or tablet present in the bowl.

U.S. Pat. No. 2,867,536 to Mead et al. describes an improved drinking straw where a soluble flavoring material is contained within an annular space contained within an inner and an outer tube. The inner tube has a bore through which liquid can be drawn. During use, the upper and lower caps are removed, the flavoring material emptied into the liquid and the flavored liquid drawn up through the inner tube and into the mouth.

U.S. Pat. No. 3,610,483 to Visconti describes a dispensing device for liquid medication that is formed in the shape of a straw. A predetermined dose of liquid medication is loaded into the straw which is then capped at both ends until the medication is dispensed when a patient removes the caps and sucks air into the device.

A variety of other oral delivery systems have been described. These include a medicated pacifier (U.S. Pat. No. 5,123,915 to Miller et al.) and a lollipop type device for a solid medicament (U.S. Pat. No. 5,223,259 to Lackney). None of these devices or the devices described previously provide for the delivery of a solid medicament into the oral cavity as a bolus dose, while avoiding the difficulties inherent in swallowing a solid system such as a tablet or a capsule or the shelf-life problems encountered when a medicine is dissolved or dispersed in a fluid, preferably an aqueous liquid.

SUMMARY OF THE INVENTION

Accordingly, in one aspect, the present invention is directed to an oral delivery system for delivering discrete units of an active agent formulation in admixture with a fluid. The system comprises a hollow active agent formulation chamber. The chamber has a first end and a second end and contains an active agent formulation in the form of discrete units. The active agent formulation comprises an active agent. The system further comprises a fluid passing active agent formulation retainer in the first end of the chamber. The retainer prevents release of the discrete units from the first end while permitting fluid entry into the chamber.

In one embodiment, the discrete units contained within the chamber are in particulate form.

In a second embodiment, the discrete units contained within the chamber are in the form of multiple active agent dosage forms.

In a second aspect, the present invention is directed to a method for orally delivering discrete units of an active agent formulation in admixture with a fluid. The method involves inserting discrete units of an active agent formulation into a hollow drug delivery chamber of a drug delivery device. The chamber has a first end and a second end. The first end of the chamber has a fluid passing active agent formulation retainer. The drug delivery device has a first and second end. The first end of the drug delivering device is inserted into a fluid and the second end is inserted into the mouth of a patient. The patient then applies suction to the second end of the device to cause delivery of the fluid and discrete units of active agent formulation into the patient's mouth.

BRIEF DESCRIPTION OF THE DRAWINGS

The figures are not drawn to scale, but are set forth to illustrate various embodiments of the invention. Like numbers refer to like structures.

FIG. 5A is a cross-sectional view.

DETAILED DESCRIPTION OF THE INVENTION

The present invention provides a device for the oral delivery of an active agent formulation in the form of discrete units that is easy to manufacture and use and that can deliver a predetermined amount of active gent. The invention also provides a method for the oral delivery of the discrete units in admixture with a fluid.

Definitions

The term "active agent formulation" intends the active agent or drug optionally in combination with pharmaceutically acceptable carriers and additional inert ingredients.

The term "discrete units" intends the active agent formulation in solid or particulate form.

An "oral dosage form" as described herein is meant the active agent formulation when placed in a discrete unit that is capable of maintaining its physical configuration and chemical integrity while housed within the delivery device.

As used herein, the terms "therapeutically effective amount" or "therapeutically effective rate" refer to the amount or rate of the active agent needed to effect the desired pharmacologic, often beneficial result.

The term "active agent formulation retainer" refers to a valve, plug or restriction, or the like that prevents passage of the active agent formulation from the device. By "fluid passing active agent formulation retainer" is intended a valve, plug or restriction or the like that allows for passage of fluids but does not allow for passage of other ingredients such as the active agent formulation that is contained in the delivery device.

The dispensing devices of the invention find use where it is inconvenient or unsafe to use solid oral dosage forms such as capsules or tablets. The devices may be particularly useful in geriatric or pediatric patient populations but they may also be useful for those who have difficulty swallowing capsules or tablets. A single delivery device or several devices can be administered to a patient during a therapeutic program.

Figures 1A, 1B, 2A:
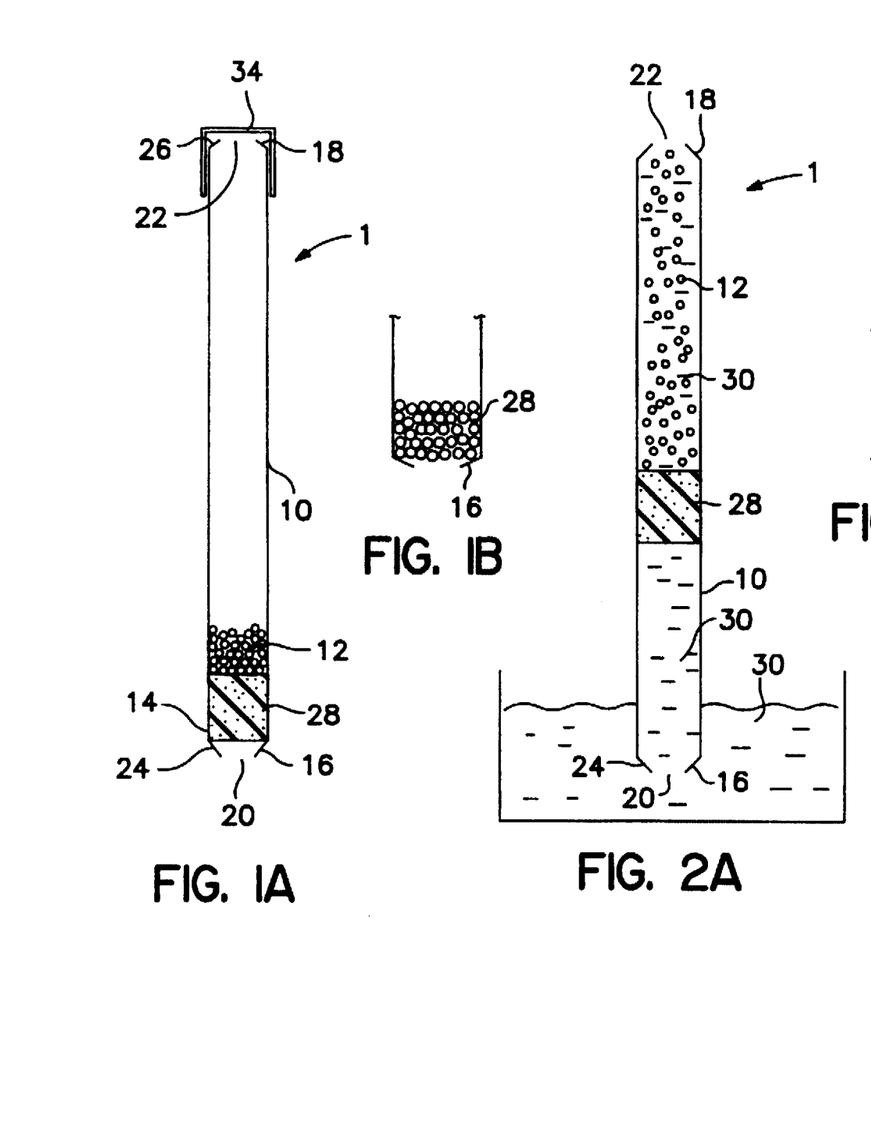
FIG. 1A is a cross-sectional view of one embodiment of the delivery device of the invention in prepared form prior to placement in a liquid medium.
FIG. 1B is an enlarged sectional view of the first end of the device of FIG. 1A.
FIG. 2A shows the device of FIG. 1A following placement in a liquid medium and delivery of a portion of the active agent formulation.

FIG. 1A depicts, in a cross-sectional view, one embodiment of the delivery device according to the invention. The device is in prepared form prior to placement in a fluid. Dispensing device 1 is shown in FIG. 1A to comprise a hollow active agent formulation chamber 10 with a first end 16 and a second end 18. Contained within chamber 10 are active agent formulation 12 and fluid passing active agent formulation retainer 14. The fluid passing active agent formulation retainer 14 comprises a restriction 24 and a one-way plug 28. The diameter of opening 20 is smaller than the plug 28. In the embodiment shown in FIG. 1A, the restriction is made by crimping the end 16 of chamber 10. Second end 18 of chamber 10 has an active agent formulation retainer 26 for preventing release of plug 28. In the embodiment shown in FIG. 1A, the retainer 26 is prepared by crimping the end 18 of chamber 10. Active agent formulation 12, which can be particles of drug, coated drug particles, or "tiny time pills", either alone or with additional carriers, is then placed in the chamber 10. End-cap 34 is placed over the second end 18 of the chamber 10 prior to use to prevent release of the active agent formulation 12. FIG. 1B is an enlarged view of plug 28, showing that, in prepared form, plug 28 essentially seals the first end 16 of the chamber 10, thereby preventing loss of active agent formulation 12 from the first end 16.

Figures 2B, 3A, 3B:
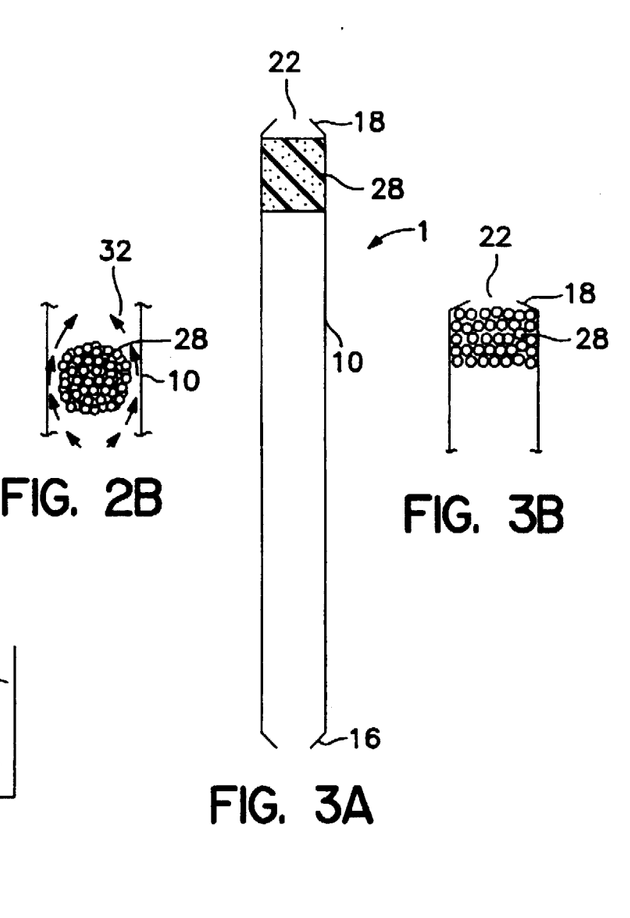
FIG. 2B is an enlarged sectional view of the middle section of the device of FIG. 2A.
FIG. 3A shows the device of FIG. 1A following complete delivery of the active agent formulation.
FIG. 3B is an enlarged sectional view of the second end of the device of FIG. 3A.

FIG. 2A shows the delivery device 1 in operation after having been placed in fluid 30. The first end 16 of the delivery device 1 is placed in the fluid 30 and the second end 18 of the device is placed in the patient's mouth. The patient sips on the second end 18 of the device and an admixture of fluid 30 and active agent formulation 12 is delivered through opening 22 and into the patient's mouth. As shown in FIG. 2B, the plug 28 serves as a one-way valve. When suction is applied through the tubular member 10, the plug 28 is deformed, thereby permitting fluid to flow around the plug 28 as shown by arrows 32. When suction is removed, the plug 28 relaxes and automatically seals the chamber 10 (see FIG. 3B). The plug 28, which has a density of less than 1, moves up the elongated tubular member, thereby aiding in delivery of the active agent formulation 12. The position of plug 28 in chamber 10 serves as an indicator of approximately how much of the active agent formulation 12 has actually been delivered.

FIG. 3A shows delivery device 1 after delivery of the active agent formulation has essentially been completed. The plug 28 is seated adjacent the opening 22 but it does not leave the chamber 10 since the diameter of the opening is less than the diameter of the plug 28 (see FIG. 3B). The position of plug 28 adjacent the opening 22 serves as an indication that the entire active agent formulation 12 has been delivered.

Figure 4:
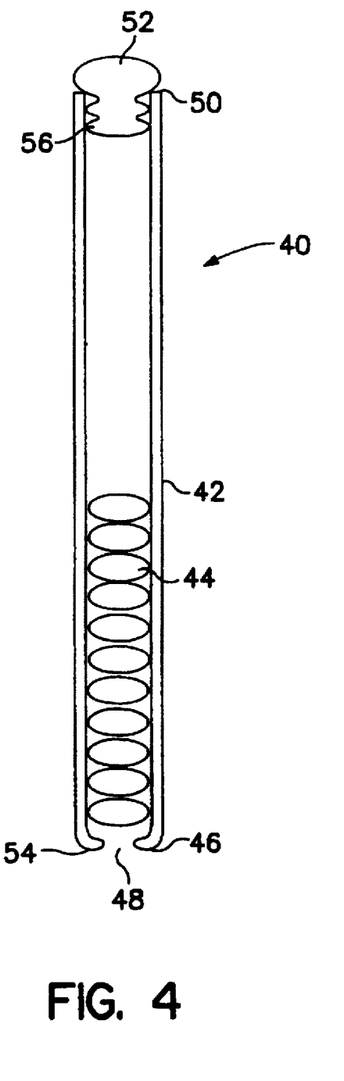
FIG. 4 is a cross-sectional view of a second embodiment of the delivery device of the invention in prepared form.

FIG. 4 depicts, in cross-sectional view, a second embodiment of the delivery device according to the invention. The device is in prepared form prior to placement in the fluid. Dispensing device 40 is shown in FIG. 4 to comprise an active agent formulation chamber 42. Contained within chamber 42 are multiple oral dosage forms 44. First end 46 of the chamber 42 has a fluid passing active agent formulation retainer 54 prepared by crimping the chamber 42 so that the diameter of the opening 48 is smaller than the dosage form 44. In this way the dosage form 44 will not fall out of the chamber 42. Second end 50 contains a active agent formulation retainer 56 that is in the form of a removable seal 52. In operation, the first end 46 of the chamber 42 is inserted into a fluid, removable seal 52 is removed and second end 50 is placed into the mouth of the patient. The patient then sips on the end 50 so that the fluid/dosage form admixture is delivered into the oral cavity and can easily be swallowed. Dosage forms 44 may be of the instant release, delayed release, continuous release or controlled release type, depending on the pattern of drug administration desired.

Figure 5A:
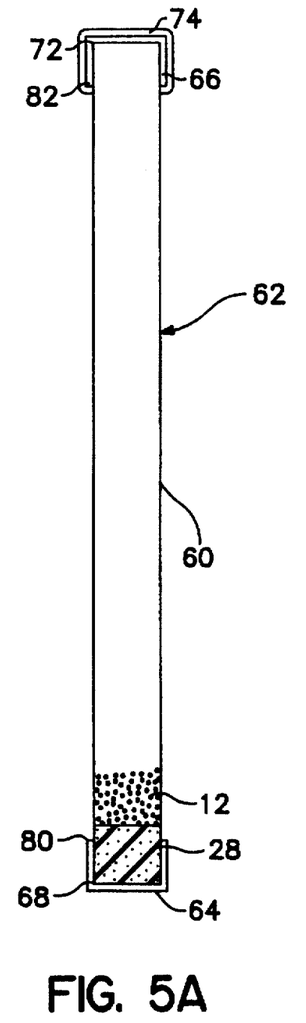
Figure 5B:
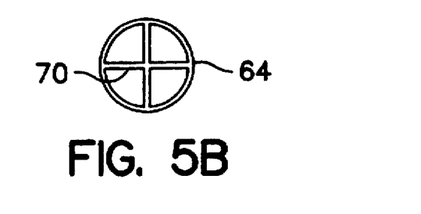
FIG. 5B is a bottom view and FIGS. 5C and 5D are top views of a third embodiment of the delivery device of the invention in prepared form.
Figure 5C:
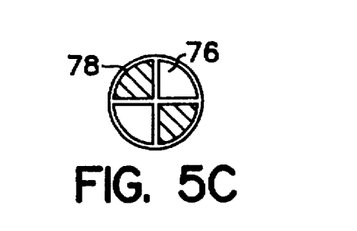
Figure 5D:
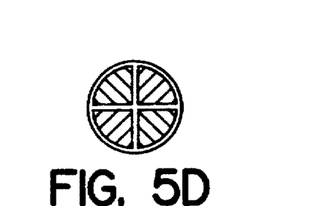

FIG. 5A is a cross-sectional view of yet another embodiment of the device of the invention in prepared form prior to placement in a fluid. In this embodiment, the active agent formulation chamber 60 of delivery device 62 is of essentially uniform diameter over its entire length. In its prepared form, the fluid passing active agent formulation retainer 80 comprises a plug 28 and an end cap 64. End cap 66 is positioned over the second end 72 end of the chamber 60 and forms the active agent formulation retainer 82. End cap 64, positioned over the first end 68 of the chamber 60, is designed to allow free passage of fluid but to prevent displacement of the one-way plug 28 from the first end 68 of chamber 60. As shown in FIG. 5B, the end cap 64 may have a cross-shaped inner member 70, however, any conveniently shaped inner member is contemplated that will allow for passage of fluid but will not permit displacement of the one-way plug 28. End cap 66, placed over the second end 72 of the chamber 60, is designed to allow free passage of liquid when suction is applied by the patient, but to provide a means for closing the end of the device prior to use. Accordingly, rotary valve 74 is placed over end cap 66. The top view of both end cap 66 and rotary valve 74 are shown in FIG. 5C. This configuration allows for free passage of fluid when the open sections 76 are aligned with each other and for prevention of fluid flow when the open sections 76 are aligned with closed sections 78. FIG. 5D is a top view of the device of FIG. 5A when the open sections 76 of the valve 74 are aligned with the closed sections 78 of the end cap 66.

Figure 6:
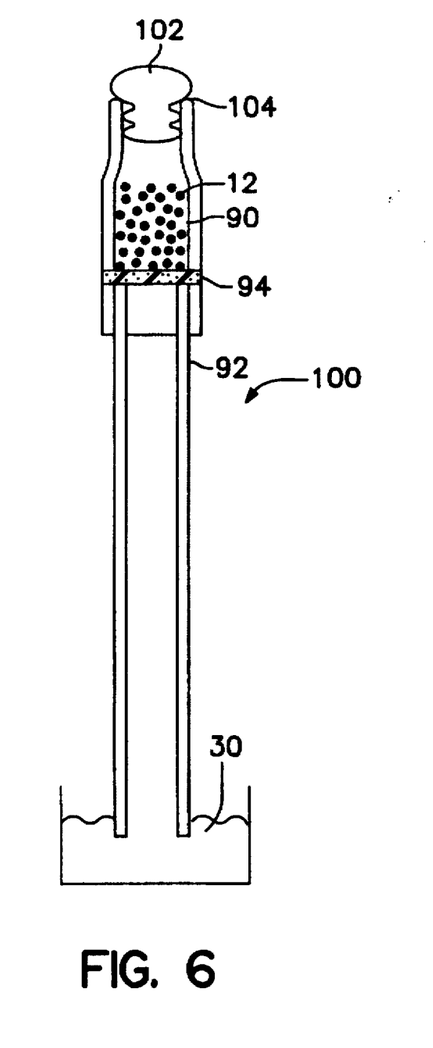
FIGS. 6–9 are cross-sectional views of other embodiments of the delivery device of the invention in prepared form.

FIG. 6 is a cross-sectional view of still another embodiment of the device of the invention in prepared form prior to placement in the fluid. In this embodiment, an active agent formulation chamber 90 is situated on top of an elongated tubular member 92 and separated by a fluid passing active agent formulation retainer 94, in this case a porous plug. When the first end 96 of the device 100 is placed in a fluid 30 and the active agent formulation retainer 102, in this case a removable seal, is removed from the second end 104 of the device, fluid can be sipped up through the elongated tubular member 92 and through the chamber 90 to form an admixture of the fluid 30 and the active agent formulation 12 contained within the active agent formulation chamber 90 prior to delivery into the oral cavity.

Figure 7:
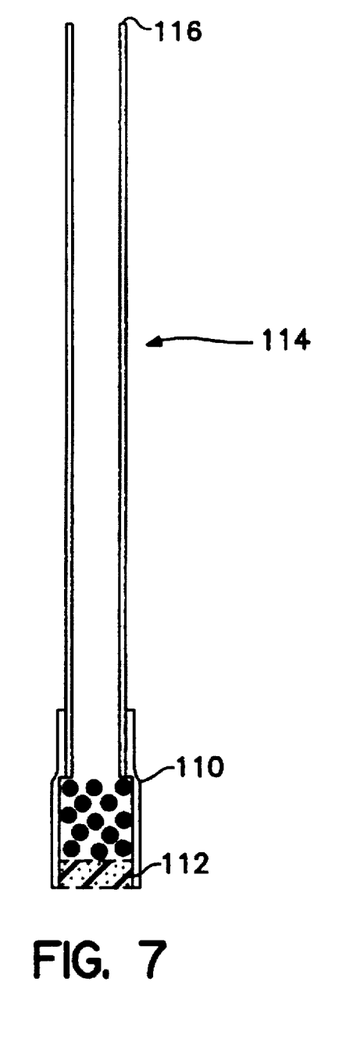

FIG. 7 is a cross-sectional view of another embodiment of the device of the invention. This embodiment is similar to that shown in FIG. 6, but the active agent chamber 110 is at the first end 112 of the device 114 rather than at the second end 116. Delivery of active agent occurs as described with regard to FIG. 6.

Figure 8:
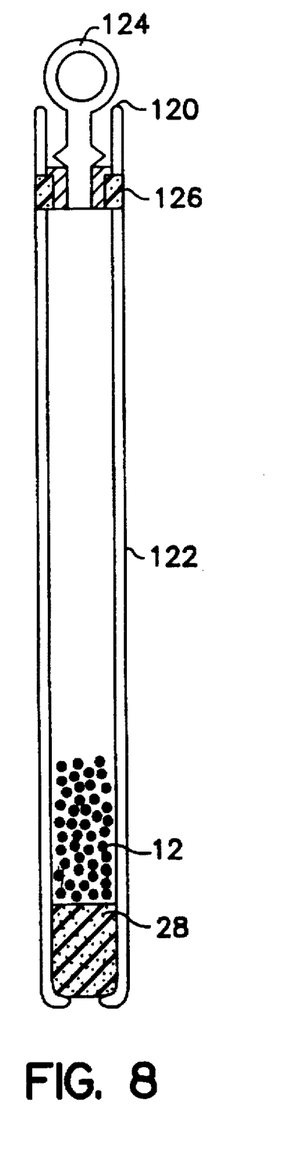

FIG. 8 is a cross-sectional view of an embodiment that is similar to that shown in FIG. 1 but the second end 120 of the active agent fomulation chamber 122 is not crimped but rather has an active agent formulation retainer 124, in this case a tab that can be pulled out, leaving behind a protrusion 126 that will prevent release of the plug 28 following delivery of the active agent formulation 12.

Figure 9:
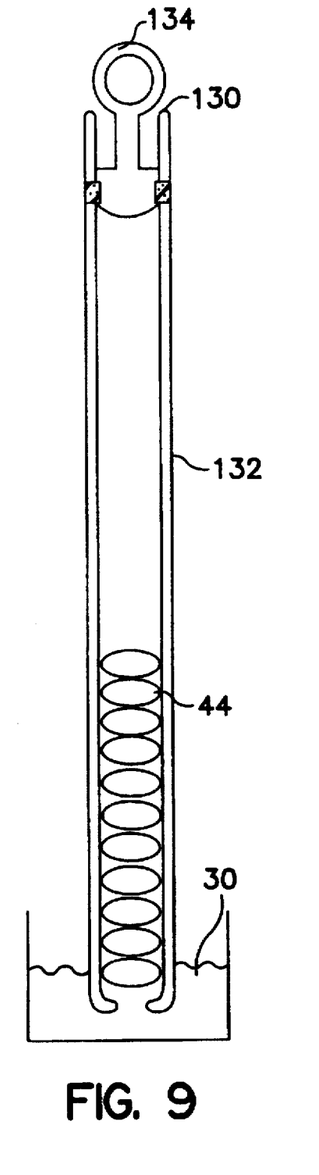

FIG. 9 is a cross-sectional view of an embodiment that is similar to that shown in FIG. 4, but rather than a removable seal, the second end 130 is sealed with a tab 134 that can be completely removed prior to placement of the device in the fluid 30 and delivery of the oral dosage forms 44.

The active agent itself may be in liquid, solid, or semisolid form. The active agent formulation that contains the active agent may contain additional material such as binders, coating materials, or stabilizers such that the formulation is formed into one or more discrete units. The discrete units may be designed in a multitude of ways to provide a specific drug delivery profile. One embodiment comprises a formulation that is in particulate form. These particulates are generally between about 50 and 2000 μm in diameter, usually between about 100–500 μm in diameter. Where the particulate has an unpleasant taste, the particulate may be taste masked by methods that are well known in the art. The particulates may be designed to provide immediate delivery of the active agent, they may be coated to provide for prolonged release or delayed pulse release of the active agent, or they may be designed to provide for a combination of immediate, pulsed and/or prolonged delivery of active agent. The particulates may be coated with an enteric coating to provide for targetted release of the active agent. In addition there may be active agent formulations that contain more than one active agent.

In other embodiments, the active agent may be in liquid form and may be contained within a soft gelatin capsule or within a solid oral dosage form.

These dosage forms may include, matrix or other types of tablets, pellets and elongated tablets where the height to diameter ratio exceeds one, capsules, elementary osmotic pumps, such as those described in U.S. Pat. No. 3,845,770, mini osmotic pumps such as those described in U.S. Pat. Nos. 3,995,631, 4,034,756, and 4,111,202, and multichamber osmotic systems referred to as push-pull and push-melt osmotic pumps, such as those described in U.S. Pat. Nos. 4,320,759, 4,327,725, 4,449,983, and 4,765,989 all of which are incorporated herein by reference.

A method for determining the release profile of active agent from solid dosage forms may be calculated as follows:

$$n=x+y+z$$

n=total number of discrete units in the device x=immediate release discrete units y=constant release discrete units z=delayed release discrete units Constant release will be obtained when x=z=0; two pulse release will occur when y=0; and constant release with an initial pulse will occur when z=0. Where none of x, y, or z=0, there will be an pulse/constant release/pulse release. Such systems provide for large capacity devices with the possibility of once a day dosing.

The term "active agent" refers to an agent, drug, compound, composition of matter or mixture thereof which provides some pharmacologic, often beneficial, effect. This includes foods, food supplements, nutrients, drugs, vitamins, and other beneficial agents. As used herein, the terms further include any physiologically or pharmacologically active substance that produces a localized or systemic effect in a patient. The active drug that can be delivered includes antibiotics, antiviral agents, anepileptics, analgesics, anti-inflammatory agents and bronchodilators, and may be inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, polysaccharides, steroids, hypnotics and sedatives, psychic energizers, tranquilizers, anticonvulsants, muscle relaxants, antiparkinson agents, analgesics, anti-inflammatories, muscle contractants, antimicrobials, antimalarials, hormonal agents including contraceptives, sympathomimetics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of active agents useful in this invention include prochlorperazine edisylate, ferrous sulfate, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-b-estradiol, ethinyl estradiol, ethinyl estradiol 3-methyl ether, prednisolone, 17-b-hydroxyprogesterone acetate, 19-nor-progesterone, norgestrel, norethindrone, norethisterone, norethiederone, progesterone, norgesterone, norethynodrel, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyidopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin and luteinizing hormone.

It is to be understood that more than one active agent may be incorporated into the active agent formulation in a device of this invention, and that the use of the term "agent" in no way excludes the use of two or more such agents.

The agents can be in various forms, such as soluble and insoluble charged or uncharged molecules, components of molecular complexes or nonirritating, pharmacologically acceptable salts.

The amount of active agent employed in the delivery device will be that amount necessary to deliver a therapeutically effective amount of the agent to achieve the desired result. In practice, this will vary widely depending upon the particular agent, the severity of the condition, and the desired therapeutic effect. However, the device is generally useful for active agents that must be delivered in fairly large doses of from about 100 mg to 5000 mg, usually in the range of from about 250 mg to about 2500 mg. However, since the devices may also be useful in pediatric patients, doses in the ranges of 25 to 250 mg are also contemplated herein.

Representative materials for forming devices including the active agent formulation chamber, the elongated tubular member, the end caps and tabs, include, without limitation, paper, plastic such as propylene/styrene copolymers, polyproylene, high density polyethylene, low density polyethylene and the like. The devices usually have an inner diameter of between about 3 and 8 mm and a wall thickness of between about 0.1 and 0.4 mm. The devices are between about 10 and 30 cm in length.

The fluid passing active agent formulation retainer permits the free flow of liquid medium but prohibits passage of the active agent formulation from the device prior to delivery. Where the retainer comprises a one-way plug or valve, the plug or valve will seal the straw at atmospheric pressure. When suction is applied, fluid will be draw around the plug and into the active agent formulation chamber. Further, the plug has a density of less than one so that it will ascend to the top as the active agent formulation is delivered into the oral cavity. When suction is no longer applied, the plug will remain in the highest position it reached during sipping. The plug may be prepared from closed cell polyethylene foam such as EthaFoam®). Other forms of one way plugs can be a balloon of elastomeric material, a one-way mechanical ball valve and the like.

The fluid that is used for suspending the active agent formulation by sipping through the active agent formulation chamber is preferably any good-tasting liquid including but not limited to water, juice, milk, soda, coffee, tea etc. Care must be taken to ensure compatibility of the fluid with the active agent formulation.

The following examples are illustrative of the present invention. They are not to be construed as limiting the scope of the invention. Variations and equivalents of these examples will be apparent to those of skill in the art in light of the present disclosure, the drawings and the claims herein.

EXAMPLES

Example 1

A delivery device according to the present invention was prepared as follows. Jumbo size straws with an inside diameter of 0.21 inches and a length of 8 inches were heat sealed at one end. The seal was partially cut off so that the "one-way" plug could not escape. The partially sealed end was enclosed by half of a size 1 hard gelatin capsule. 600 mg of membrane coated potassium chloride microparticles with a particle size of about 0.5 mm from a Micro-K Extencap® (A. H. Robins) were placed inside the open end of the straw. A "one-way" plug made of closed cell polyethylene foam, Microfoam® (DuPont) was trimmed to snugly fit inside the straw. The plug was then placed inside the straw, on top of the Micro-K particles.

During operation, the plug end of the straw was placed into a glass of water and the protective gelatin capsule on the top of the straw was removed. By slowly applying suction through the partially sealed end of the straw, the 600 mg of Micro-K particles were sucked into the mouth and easily swallowed.

Example 2

The device was prepared according to Example 1, but instead of Micro-K, the contents of a Contact® 12 hour capsule (SmithKline Beechem), an over the counter continuous action nasal decongestant/antihistamine containing 25 mg phenylpropanolamine and 12 mg chlorpheniramine maleate were inserted into the straw. The microparticulates were in the range of between about 0.5 and 1.0 mm. The particulates were sucked into the mouth as described in Example 1.

Example 3

A delivery device according to the present invention was prepared as follows. Jumbo size straws with an inside diameter of 0.21 inches and a length of 6 inches were heat sealed at one end. The seal was partially cut off so that the orifice had a diameter of less than 5 mm.

Small elementary osmotic pumps of calcium ascorbate were prepared as follows. The core compartment was formed from 50 mg of calcium ascorbate, 2.7 mg polyvinyl pyrrolidone and 0.6 mg of magnesium stearate. The ingredients were thoroughly mixed and pressed in a Manesty press with a 3/16inch round punch using a pressure head of 1 1/2tons. A semipermeable wall of 5 mg was formed by blending 80% cellulose acetate having an acetyl content of 39.0%, 10% sorbitol and 5% polyethylene glycol 400. The solution was spray coated onto the core compartment with a solvent consisting of 714 ml of acetone and 186 ml of water in an air suspension machine. The coated osmotic tablet was dried for 72 hours at 50° C. A 0.2 mm orifice was hand drilled into the wall.

Twenty of the small osmotic systems with a total dose of 1000 mg of calcium ascorbate were place inside the straw from the open end. The partially sealed end of the straw was placed into a glass of water. The twenty small osmotic dosage forms were easily sipped into the mouth with a small amount of suction to provide a prolonged release of Vitamin C.

The above description has been given for ease of understanding only. No unnecessary limitations should be understood therefrom, as modifications will be obvious to those skilled in the art.

We claim:

1. An oral active agent delivery system for delivering to a patient discrete units of active agent formulation in admixture with a fluid, said system comprising:

a tubular active agent formulation chamber, said chamber having a first end and a second end and containing an active agent formulation in the form of discrete units, said first end being adapted for fluid communication with a fluid and said second end being adapted for oral application of suction by the patient; and a fluid passing active agent formulation retainer in said active agent formulation chamber for preventing release of the discrete units from the first end of the chamber while permitting fluid entry into the chamber, said retainer being transportable toward said second end of said chamber with the fluid entering said first end of said chamber upon application of suction at said second end.

2. The delivery system of claim 1 further comprising an active agent formulation retainer in the second end of the active agent formulation chamber for preventing release of said active agent formulation from said second end prior to use.

3. The delivery system of claim 2 wherein said active agent formulation retainer in the second end of the chamber comprises a rotary valve.

4. The delivery system of claim 2 wherein said active agent formulation retainer in the second end of the chamber comprises a narrowing in the second end of the chamber.

5. The delivery system of claim 2 wherein said active agent formulation retainer in the second end of the chamber comprises a removable end cap.

6. The delivery system of claim 1 wherein said discrete units are selected from the group consisting of particulates, oral dosage forms and combinations thereof.

7. The delivery system of claim 1 wherein said discrete units provide for prolonged delivery of the active agent in said formulation.

8. The delivery system of claim 1 wherein said discrete units provide for immediate delivery of the active agent in said formulation.

9. The delivery system of claim 1 wherein said discrete units provide for delayed pulsed delivery of said active agent in said formulation.

10. The delivery system of claim 1 wherein said discrete units comprise oral dosage forms that comprise an osmotic layer and an active agent layer.

11. The delivery system of claim 1 further wherein said active agent formulation retainer comprises a one-way plug.

12. The delivery system of claim 11 wherein the position of the plug is an indicator of the extent of active agent delivery.

13. The delivery system of claim 1 further comprising an end cap concentrically surrounding the first end of the chamber.

14. The delivery system of claim 1 wherein said active agent formulation comprises an active agent selected from the group consisting of antibiotics, antiviral agents, anepileptics, analgesics, anti-inflammatory agents and bronchodilators.

15. A method for observing the delivery to a patient of a dose of active agent formulation in admixture with a liquid from a delivery system comprising a tubular member containing the active agent formulation and a transportable active agent formulation retainer positioned between the active agent formulation and the liquid, wherein the method comprises:

observing a first position of the active agent formulation retainer within the tubular member and observing a second position of the retainer within the tubular member after suctioning liquid through the tubular member upon oral application of sucking by the patient, and removing the suction.

* * * * *

UNITED STATES PATENT AND TRADEMARK OFFICE
CERTIFICATE OF CORRECTION

PATENT NO.   : 5,780,058
DATED        : July 14, 1998
INVENTOR(S)  : Patrick S.-L. WONG et al.

It is certified that error appears in the above-identified patent and that said Letters Patent is hereby corrected as shown below:

Title page:

Under  "[22] Filed: Jul. 19, 1996" insert – RELATED U.S. APPLICATION DATA [60] Provisional Application No. 60/001,319 July 21, 1995. --;

Before column 1, line 4, insert -- Cross Reference to Related Applications This application claims the priority of provisional patent application Serial No. 60/001,319 filed July 21, 1995. --.

Signed and Sealed this

Fourth Day of May, 1999

Attest:

Q. TODD DICKINSON

*Attesting Officer*    Acting Commissioner of Patents and Trademarks